US00PP32185P2

(12) United States Plant Patent
Brazelton et al.

(10) Patent No.: US PP32,185 P2
(45) Date of Patent: Sep. 15, 2020

(54) *VACCINIUM* PLANT NAMED 'FC12-187'

(50) Latin Name: ***Vaccinium (angustifolium* x *myrsinites)* x *corymbosum* hybrid**
Varietal Denomination: FC12-187

(71) Applicant: THE CONARD-PYLE COMPANY, West Grove, PA (US)

(72) Inventors: David M. Brazelton, Walterville, OR (US); Adam L. Wagner, Eugene, OR (US)

(73) Assignee: THE CONARD-PYLE COMPANY, West Grove, PA (US)

( * ) Notice: Subject to any disclaimer, the term of this patent is extended or adjusted under 35 U.S.C. 154(b) by 0 days.

(21) Appl. No.: 16/602,377

(22) Filed: Sep. 26, 2019

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
CPC ..... A01H 5/08; A01H 6/36
See application file for complete search history.

(56) References Cited

U.S. PATENT DOCUMENTS

PP25,467 P3 4/2015 Brazelton et al.

*Primary Examiner* — Annette H Para
(74) *Attorney, Agent, or Firm* — Panitch Schwarze Belisario & Nadel LLP

(57) ABSTRACT

A new and distinct variety of *Vaccinium* plant, herein referred to by its cultivar name, 'FC12-187', is provided which displays white-colored inflorescence. The foliage is medium green colored. The vegetation is moderately vigorous and the growth habit is mounded to weeping. A good crop load of small, dark colored fruit is formed.

2 Drawing Sheets

Figure 1:
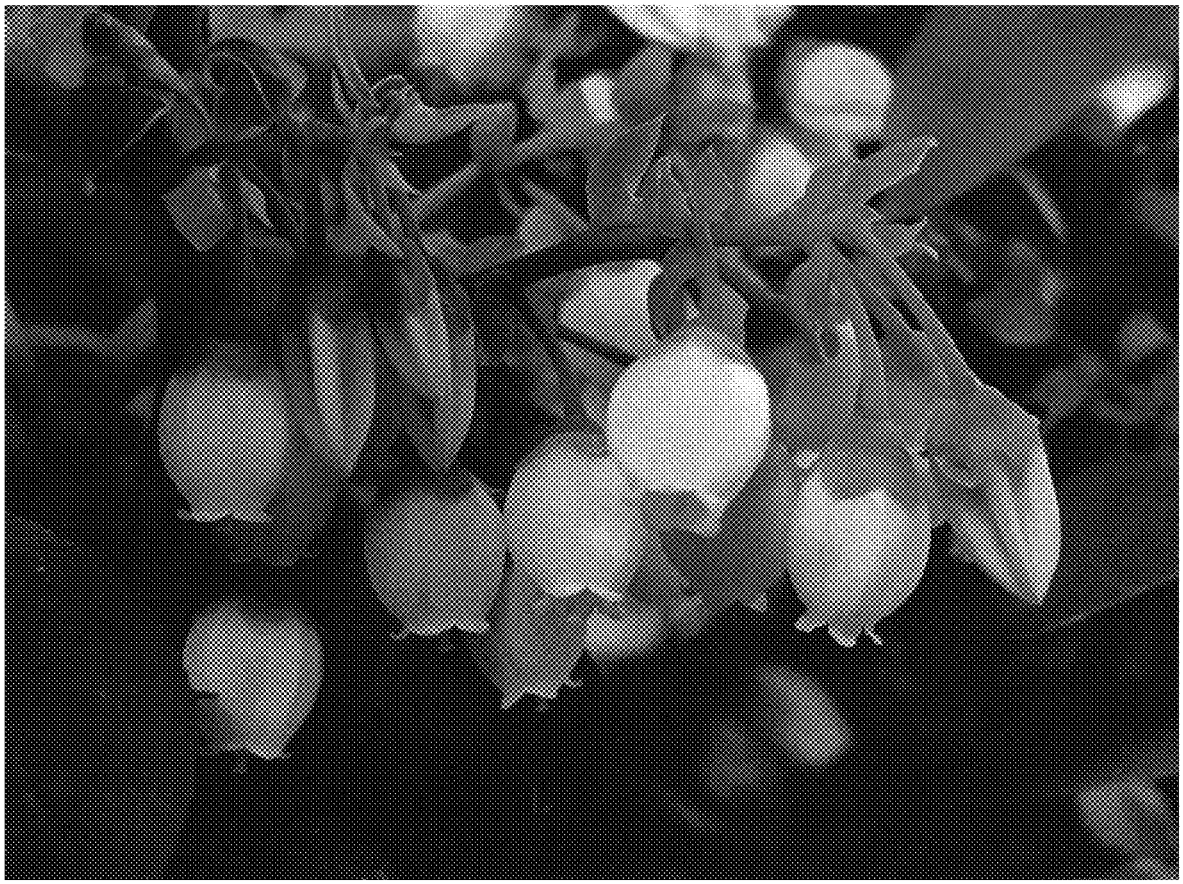

Botanical/commercial classification:

Latin name of genus and species of plant claimed: *Vaccinium* (*angustifolium* x *myrsinites*) x *corymbosum* hybrid.

Variety denomination: 'FC12-187'.

BACKGROUND OF THE INVENTION

The present invention relates to a new and distinct cultivar of *Vaccinium* plant botanically known as *Vaccinium* (*angustifolium* x *myrsinites*) x *corymbosum* hybrid and hereinafter referred to by the cultivar name 'FC12-187'.

The new cultivar was created in a controlled breeding program in Lowell, Oreg. during May 2010. The objective of the breeding program was the development of superior *Vaccinium* cultivars that meet the evolving needs of the blueberry and home enthusiast industries.

The new *Vaccinium* cultivar is the result of cross-pollination. The female parent (i.e., seed parent) of the new cultivar is 'NC-4339', a non-introduced, non-patented breeder seedling. The male parent (i.e., pollen parent) of the new cultivar is 'ZF09-233', a non-introduced, non-patented breeder seedling.

The parentage can be summarized as follows:

'NC-4339' x 'ZF09-233'

The new cultivar was obtained and selected as a single flowering plant within the progeny of the above stated cross-pollination during July 2012 in a controlled environment in Lowell, Oreg.

Asexual reproduction of the new cultivar by softwood stem cuttings since 2012 in Lowell, Oreg. has demonstrated that the new cultivar reproduces true to type with all of the characteristics, as herein described, firmly fixed and retained through successive generations of such asexual propagation.

SUMMARY OF THE INVENTION

The new cultivar of the present invention possesses the following combination of characteristics, which have been repeatedly observed and can be used to distinguish 'FC12-187' as a new and distinct cultivar of *Vaccinium* plant:

(a) forms white colored inflorescences,
(b) exhibits medium green foliage,
(c) forms moderately vigorous, mounded to weeping growth habit, and
(d) produces a good crop load of small dark colored fruit.

The new variety can be readily distinguished from its ancestors. More specifically, 'NC-4339' (i.e., seed parent) exhibits a less prostrate growth habit and more red bark color. Additionally, 'ZF09-233' (i.e., pollen parent) exhibits a less dense canopy and less uniform growth. Moreover, the new variety can be readily distinguished from non-parental related similar varieties. Of the many commercially available *Vaccinium* cultivars, the most similar in comparison to the new cultivar is 'ZF08-095' (U.S. Plant Pat. No. 25,467). However, plants of the new cultivar differ from plants of 'ZF08-095' in at least the following characteristics:

1. Plants of the new cultivar have a wide and low growth habit, whereas plants of 'ZF08-095' have a round growth habit;
2. Plants of the new cultivar have leaves that are lighter green and less glossy than plants of 'ZF08-095'.

BRIEF DESCRIPTION OF THE PHOTOGRAPH

The accompanying photographs show, as nearly true as it is reasonably possible to make the same in color illustrations of this type, typical specimen of the new variety. The illustrated *Vaccinium* plant of the new variety in FIG. 1 was approximately two years of age and was grown in Cochranville, Pa. in April 2019. The illustrated *Vaccinium* plant of the new variety in FIG. 2 was approximately two years of age and was grown outdoors in a hanging basket in Lowell, Oreg. in July 2017.

FIG. 1—illustrates a close-up view of a flower cluster of 'FC12-187'.

Figure 2:
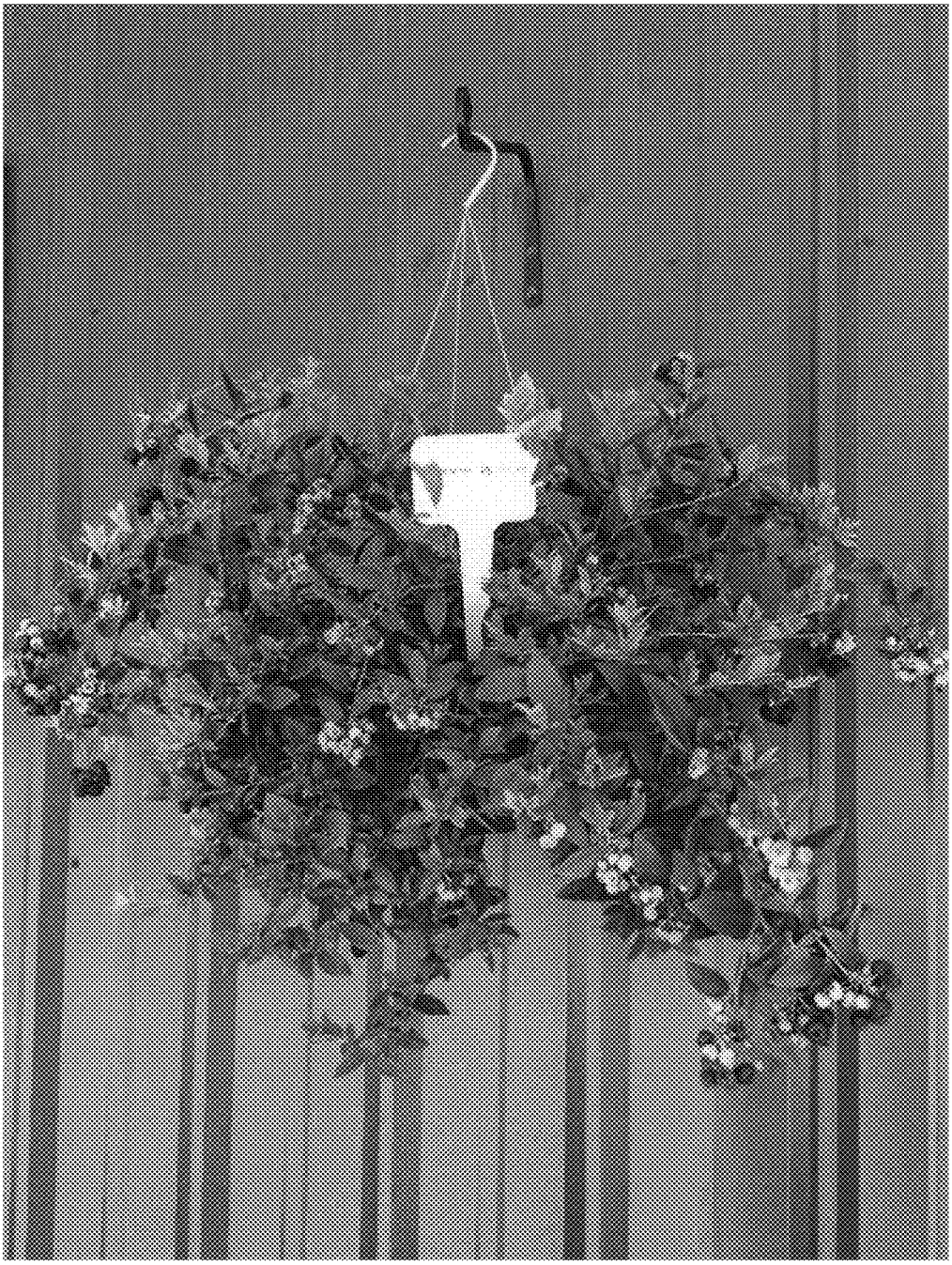

FIG. 2—illustrates a side view of a plant of 'FC12-187'.

DETAILED BOTANICAL DESCRIPTION

The chart used in the identification of colors described herein is that of The Royal Horticultural Society (R.H.S. Colour Chart, London, England, 2015 edition), except where general color terms of ordinary significance are used. The terminology which precedes reference to the chart has been added to indicate the corresponding color in more common terms. The color values were determined under natural light conditions in Cochranville, Pa. Measurements and numerical values represent averages of typical plants.

Plant:

*Growth habit and general appearance.*—Moderately vigorous, wide and low growth habit.

*Size.*—Height: from soil level to top of plant plane is approximately 35.0 cm. Width: approximately 60.0 cm.

*Branching habit.*—Freely branching. Pinching enhances branching. Quantity of lateral branches per plant: approximately 6 main branches.

*Branch.*—Strength: strong. Length: approximately 25.0 cm. Diameter: approximately 3.0 mm. Length of central internode: approximately 2.0 cm. Texture: mostly smooth with some rough areas where the wood is starting to become harder. Color of mature stems: commonly mostly Yellow-Green Group 146B with some coloring of near Greyed-Orange Group 177B and 177A where the wood is starting to become harder.

Foliage:

*General description.*—Fragrance: none detected. Form: simple. Arrangement: alternate.

*Leaves.*—Shape: elliptic. Margin: entire. Apex: acute. Base: cuneate. Venation pattern: pinnate. Length of mature leaf: approximately 4.8 cm. Width of mature leaf: approximately 2.3 cm. Texture of upper and lower surfaces: glabrous and glossy. Color of upper and under surfaces of young foliage: commonly near Yellow-Green Group 144A with indistinguishable venation. Color of upper surface of mature foliage: commonly near Green Group 137A with venation of near Green Group 137B. Color of lower surface of mature foliage: commonly near Green Group 137C with venation of near Green Group 137D.

*Petiole.*—Length: approximately 2.0 mm. Diameter: approximately 1.0 mm. Texture: glabrous. Color: commonly near Yellow-Green Group 144B.

Flowering:

*Flowering season.*—Flowers in spring in southeastern Pennsylvania.

*Lastingness of individual inflorescence on the plant.*—Approximately one week.

Flower:

*General description.*—Shape: urceolate. Quantity per plant: approximately 100 fully open on a plant at a given time. Fragrance: very slight, sweet. Aspect: pendulous.

*Bud just before opening.*—Shape: oval. Length: approximately 1.1 cm. Diameter: approximately 0.5 cm. Color: commonly close to Green-White Group 157B.

*Corolla.*—Color: commonly near White Group 155A. Length: approximately 1.0 mm. Width: approximately 6.0 mm. Aperture width: approximately 4.0 mm.

*Calyx.*—Shape: star-shaped. Depth: approximately 4.0 mm. Diameter: approximately 6.0 mm.

*Sepals.*—Quantity: 5. Shape: ovate. Margin: entire. Apex: acute. Base: fused. Length: approximately 4.0 mm. Width: approximately 2.0 mm. Texture of upper surface: glabrous. Texture of lower surface: glabrous. Color of upper and lower surfaces: commonly near Green Group 143B.

*Reproductive organs.*—

*Androecium.*—Stamen quantity per flower: approximately 10. Stamen length: approximately 4.0 mm. Anther shape: narrow oblong. Anther length: approximately 1.0 mm. Anther color: commonly near Greyed-Orange Group N167A. Pollen amount: not observed.

*Gynoecium.*—Pistil quantity: 1 per flower. Pistil length: approximately 1.2 cm. Stigma shape: flat disc. Stigma color: commonly near Yellow-Green Group 145A. Style length: approximately 1.0 mm. Style color: commonly near Yellow-Green Group 145B. Ovary length: approximately 2.0 mm. Ovary color: commonly near Yellow-Green Group 146C.

Fruit:

*Date of* 50% *maturity.*—July in Southeastern Pennsylvania.

*Fruit development period.*—80 to 85 days. Fruiting on one-year old shoots, not found on current season wood in most circumstances.

*Berry color.*—Commonly near Black Group 202A.

*Berry surface wax abundance.*—Low.

*Fruit bloom intensity.*—Weak.

*Berry flesh color.*—Commonly near Greyed-Green Group 198C.

*Berry size.*—Height from calyx to scar: 1.0 cm. Diameter: 1.8 cm.

*Berry shape.*—Semi-spherical.

*Berry firmness.*—Medium firm.

*Berry flavor and texture.*—Tart flavor, smooth to grainy texture.

*Suitability of mechanical harvesting.*—Not suitable.

*Uses.*—Intended for home gardens, container gardening, and/or ornamental uses.

Seed:

*Seed abundance in fruit.*—Medium to heavy, with approximately 40 seeds per berry.

*Seed color.*—Commonly near Greyed-Orange Group 165B.

*Seed size.*—1.5 mm long; 1.0 mm wide.

Development:

*Disease and pest resistance.*—Resistance to pathogens and pests common to *Vaccinium* has not been observed.

*Commercial crop time.*—Approximately one year from a rooted cutting to finish in a one-gallon container.

*Hardiness.*—USDA Zone 5.

The new cultivar has not been observed under all possible environmental conditions to date. Accordingly, it is possible that the phenotype may vary somewhat with variations in the environment, such as temperature, light intensity, and day length, without, however, any variance in genotype.

We claim:

1. A new and distinct cultivar of *Vaccinium* plant characterized by the following combination of characteristics:

(a) forms white colored inflorescences, (b) exhibits medium green foliage, (c) forms moderately vigorous, mounded to weeping growth habit, and (d) produces a good crop load of small dark colored fruits; substantially as herein shown and described.

* * * * *